United States Patent

Fellner et al.

Patent Number: 4,636,518
Date of Patent: Jan. 13, 1987

[54] IMIDAZOLE DERIVATIVES AND PHARMACEUTICAL COMPOSITIONS

[75] Inventors: Peter J. Fellner, Marlow; Mun F. Lai, Maidenhead; Thakorbhai P. Patel, High Wycombe, all of England

[73] Assignee: G. D. Searle & Co., Skokie, Ill.

[21] Appl. No.: 746,684

[22] Filed: Jun. 20, 1985

Related U.S. Application Data

[63] Continuation of Ser. No. 606,808, May 3, 1984, abandoned, which is a continuation of Ser. No. 363,180, Mar. 29, 1982, abandoned.

[30] Foreign Application Priority Data

Apr. 13, 1981 [GB] United Kingdom ................ 8111614

[51] Int. Cl.$^4$ ................ A61K 31/415; C07D 405/12
[52] U.S. Cl. ................ 514/397; 548/336; 548/341; 514/338; 514/341
[58] Field of Search ................ 548/336, 341; 514/397, 514/399

[56] References Cited

U.S. PATENT DOCUMENTS 4,036,970 7/1977 Walker et al. ................ 548/341
4,229,459 10/1980 Krämer et al. ................ 548/341

FOREIGN PATENT DOCUMENTS 2054560 2/1981 United Kingdom .

Primary Examiner—Robert W. Ramsuer
Attorney, Agent, or Firm—Steven M. Odre

[57] ABSTRACT

Compounds of the general formula:

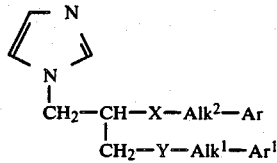

and acid addition salts thereof;

in which Ar and Ar$^1$ which may be the same or different, each represent an aromatic radical which may be substituted one or more times by substituents selected from the following:
halogen;
lower alkyl;
lower alkoxy;
alkylenedioxy;
aralkoxy;
aryloxy;
trihalomethyl;
carboxy;
carboxyalkyl;
cyano;
carboxamido;
di-lower alkylamino;
nitro; and
lower alkyl sulphonyl provided that one of the groups Ar and Ar$^1$ carries at least one alkoxy, alkylenedioxy, carboxy or carboxyalkyl substituent; and Alk$^1$ and Alk$^2$, which may be the same or different, each represent an alkylene group containing from 1 to 8 carbon atoms which may be substituted one or more times by lower alkyl;

X and Y which may be the same or different represent oxygen, nitrogen or sulphur; and in which the imidazole ring may be substituted by one or more lower alkyl substituents have antithrombotic activity. A representative compound is 1-[2-[(4-methoxyphenyl)methoxy]-3-[(4-methoxyphenyl)methoxy]propyl]-1H-imidazole.

7 Claims, No Drawings

IMIDAZOLE DERIVATIVES AND PHARMACEUTICAL COMPOSITIONS

This is a continuation of application Ser. No. 06/606,808, filed May 3, 1984, abandoned, which is a continuation of application Ser. No. 06/363,180 filed Mar. 29, 1982, now abandoned.

This invention relates to imidazole derivatives, the production thereof, to compositions containing them and to their use in pharmacy.

We have found that compounds of the general formula:

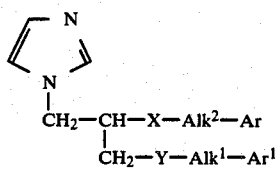

I in which Ar and Ar¹ which may be the same or different, each represent an aromatic radical which may be substituted one or more times by substituents selected from the following list:
 halogen;
 lower alkyl;
 lower alkoxy;
 alkylenedioxy;
 aralkyloxy;
 aryloxy;
 trihalomethyl;
 carboxy;
 carboxyalkyl;
 cyano;
 carboxamido;
 di-lower alkylamino;
 nitro; and
 lower alkyl sulphonyl
provided that one of the groups Ar and Ar¹ carries at least one alkoxy, alkylenedioxy, carboxy or carboxyalkyl substituent; Alk¹ and Alk² which may be the same or different each represents an alkylene group containing from 1 to 8 carbon atoms which may be substituted one or more times by lower alkyl; X and Y which may be the same or different represent oxygen, nitrogen or sulphur; and in which the imidazole ring may be further substituted by one or more lower alkyl substituents. These compounds and acid addition salts of such compounds have marked pharmacological activity, in particular as antithrombotics.

The invention therefore provides such compounds. It includes all optical isomers and racemic mixtures thereof.

The antithrombotic activity of the compounds of the invention has been determined by their ability to inhibit production of thromboxane $A_2$ ($TxA_2$) by blood platelets the synthesis of which is an important factor in the aggregation of platelets and the initiation of thrombosis (R. J. Gryglewski, CRC Crit. Rev. Biochem., (1980), 7(4), 291).

Thus, there is evidence that thrombosis is determined by the balance of products derived from prostaglandin cyclic endoperoxides between the thrombogenic $TxA_2$ released on platelet aggregation and the thrombolytic prostacyclin ($PGI_2$) formed in the vessel walls. Blocking or reducing the production of $TxA_2$ is useful in the treatment and prophylaxis of thrombosis.

Standard in vitro and in vivo pharmacological test-methods can be employed in assessing the antithrombotic activity of the compounds according to the invention.

For example the compound of Example 1 was found in in vitro tests to inhibit
 (i) the generation of thromboxane $A_2$ as determined by radioimmuno-assay of its stable metabolite, $TxB_2$ (New England Nuclear, Thromboxane $B_2$ [$^3$H] RIA kit, Catalogue No. NEK 007; and
 (ii) the aggregation of human platelet rich-plasma (G. V. R. Born et al, Nature, (1962), 194, 927).

Furthermore, the compound of Example 1 at concentrations equivalent to these which inhibit $TxA_2$ formation was found not to significantly effect production of prostacyclin in cultured endothelial cells as determined by ratioimmuno-assay of the stable metabolite of prostacyclin, 6-keto $PGF_{1\alpha}$ (New England Nuclear 6-keto $PGF_{1\alpha}$RIA kit, Catalogue No. NER 008).

In addition, in vivo tests carried out of platelet aggregation in the male retired breeder rat model (R. N. Saunders et al, Lab. Animal Sci. (1977) 27, 757) have shown compounds of formula 1 are more active than the clinically prescribed antiaggregatory compounds such as aspirin, dipyridamole and sulphinpyrazone.

The active compounds are useful wherever it is desired to inhibit platelet aggregation and/or to reduce the adhesive character of platelets, and consequently to treat or prevent the formation of thrombosis in mammals, including man. For example, the compounds may be useful in the treatment and prevention of myocardial infarcts, cerebrovascular thrombosis, ischaemic peripheral vascular disease and thrombo-embolic microangiopathy; to treat and prevent post-operative thrombosis; and to promote patency of vascular grafts following surgery; they may also be useful in the prevention and treatment of migraine.

The compounds according to the invention have at least one alkoxy, alkylenedioxy, carboxy or carboxyalkyl substituent on one of the groups Ar and Ar¹. The alkoxy group preferably contains 1-6 carbon atoms, in particular 1-4 carbon atoms. Specific alkoxy groups are methoxy and ethoxy. The alkylenedioxy group preferably contains 1-3 carbon atoms in the alkylene chain. A specific alkylenedioxy substituent is methylenedioxy. The carboxyalkyl group is preferably carboxy lower alkyl, in particular those wherein alkyl is methyl or ethyl.

The groups Alk¹ and Alk² preferably contain 1 to 4 carbon atoms in the alkylene chain.

The term 'lower' as used herein to apply to alkyl or alkoxy groups, or moieties containing them, means that such groups, preferably contain 1 to 6, in particular 1 to 4 carbon atoms.

By the term aryloxy as used herein we mean in particular phenoxy. Also by the term aralkyloxy as used herein we mean in particular benzyloxy.

Preferred compounds according to the invention are those in which Ar and Ar¹ are phenyl, naphthyl, pyridyl, furanyl or thienyl, substituted as specified above.

Preferably the alkoxy, alkylenedioxy, carboxy or carboxyalkyl substituent is situated on the group Ar or on both groups Ar and Ar¹. Preferred meanings for the group Ar are phenyl, furanyl, thienyl or pyridyl optionally substituted by one or more of the following substituents, namely, lower alkoxy, methylenedioxy, lower alkyl, carboxy and carboxyalkyl.

Specific preferred compounds according to the invention are those, the preparation of which, is described in the Examples.

The compounds of the general formula I, according to the invention may be prepared by reacting a compound of the formula (II):

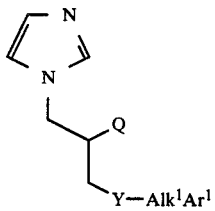                                    II in which Y, Alk$^1$ and Ar$^1$ have the meanings given hereinbefore and in which the imidazole ring may be substituted with one or more lower alkyl substituents with a compound of the general (III):

Q$^1$Alk$^2$Ar in which Q represents a group of the formula XH in which X has the meaning given hereinbefore and Q$^1$ represents a nucleophilic-displaceable group or vice versa and Alk$^2$ and Ar have the meanings given hereinbefore.

This process may also be applied to the production of a compound of formula I in which X, Y, Alk$^1$, Alk$^2$, Ar and Ar$^1$ have the meanings given hereinbefore, with the proviso that X—Alk$^2$—Ar is identical to Y—Alk$^1$—Ar$^1$, which comprises reacting a compound of the general formula IIa:

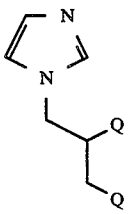                                    IIa in which Q has the meaning given hereinbefore with an appropriate amount of a compound of the formula III:

Q$^1$Alk$^2$Ar                                    III in which Q$^1$ has the meaning given hereinbefore. The compounds may be isolated as such or as a pharmaceutically acceptable acid addition salt or one such salt may be converted to another.

Thus, the compounds of formula I where X is oxygen may be prepared by reacting a compound of the general formula (II):

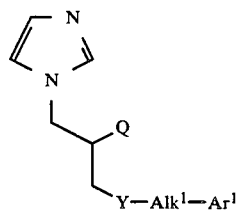                                    II in which —Q is —XH and X is oxygen and Alk$^1$, Y and Ar$^1$ are defined as hereinbefore and the imidazolyl ring may be further substituted with a compound of the general formula III:

Q$^1$—Alk$^2$—Ar                                III in which Q$^1$ represents a suitable nucleophilic-displaceable group such as a halogen atom or a mesylate, tosylate etc., and Alk$^2$ and Ar are defined as hereinbefore. The product may be isolated as the base or as an acid addition salt. The reaction is preferably carried in the presence of a suitable strong base, in particular an alkali metal hydride such as sodium hydride in an anhydrous aprotic organic solvent under an inert atmosphere. The reaction may be conducted at either room temperature (15°-20° C.) or to somewhat elevated temperature (of the order of 75° C.).

The compounds of formula II may be prepared from the parent substituted oxirane of the general formula (IV):

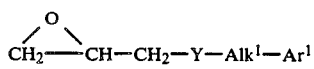                                    IV by reacting these with imidazole or substituted imidazole, which is preferably in the form of an alkali metal salt, e.g. as the sodium salt. The compound of formula IV may be obtained by reaction of a halohydrin of the formula (V):

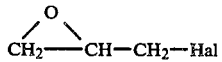                                    V in which Hal represents halogen with a compound of the formula (VI):

Ho—Alk$^1$—Ar$^1$                                 VI where Alk$^1$, and Ar$^1$ are defined as hereinbefore preferably in the presence of a suitably strong base such as sodium hydride as described above.

When X=NH compounds of formula I may be prepared by reacting a compound of the general formula II in which Q=XH where X=NH and Alk$^1$, Y and Ar$^1$ are defined as hereinbefore with a compound of general formula III in which Q$^1$, Alk$^2$ and Ar are defined as hereinbefore. The product may be isolated as the base or as an acid addition salt. The reaction is preferably carried out in the presence of a base such as triethylamine in an anhydrous aprotic solvent and advantageously at a temperature of the order of 80° C.

The compounds of formula II in which X=NH may be prepared by reduction of compounds of formula VII below with suitable reducing agents e.g. lithium aluminum hydride in an inert solvent. The compound of formula (VII):

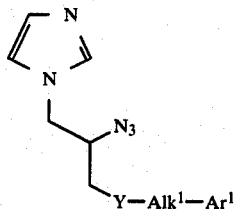

may be obtained by reaction of a mesylate (R=CH$_3$) or a tosylate (R=4—CH$_3$C$_6$H$_4$) of general formula VIII below with an alkali azide (e.g. sodium azide) in an aprotic solvent at elevated temperature (e.g. dimethylformamide at 100° C.).

Compounds of formula (VIII):

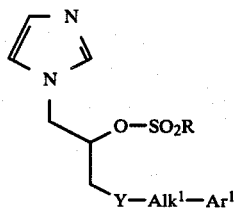

may be prepared from the compound of general structure II in which X=O (Q=OH) by reaction with either methyl sulphonyl chloride or p-toluene sulphonyl chloride using standard conditions.

The compounds of general formula I in which X=S may be prepared by reacting compounds of formula VIII above in which Alk$^1$, Ar, R and Y are as hereinbefore defined, with a mercaptan of the formula

Q$^1$—Alk$^2$—Ar    IX where Alk$^2$ and Ar are as hereinbefore defined and Q$^1$=SH preferably in the presence of a suitably strong base (e.g. sodium hydride) in an inert solvent (e.g. dimethoxyethane).

The compounds of general structure I can be prepared as the individual optical isomers for instance by synthesis from an appropriate starting material of known optical integrity. Thus the compound of general formula X having S-stereochemistry in which Ar, Ar$^1$, Alk$^1$ and Alk$^2$ are defined as hereinbefore, with the proviso that Ar=Ar$^1$ and Alk$^1$=Alk$^2$,

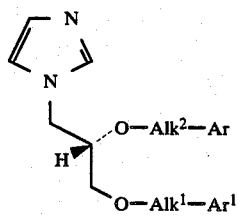

may be obtained by reacting the corresponding S-diol (XI):

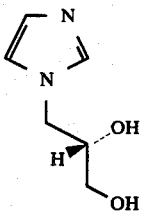

with two equivalents of the compound of general formula III defined hereinbefore in which Ar, Alk$^2$ and Q$^1$ are as hereinbefore defined. The reaction is preferably carried out in the presence of a suitable strong base, such as sodium hydride in an anhydrous aprotic solvent under an inert atmosphere. Where Ar or Ar$^1$ contains a carboxy substituent it can be derived by the base hydrolysis of the parent ester, that is the compound in which the substituent is carboxy alkyl.

The diol of structure XI may be obtained by reacting the known S-isopropylidene glycerol, 4-methylphenyl sulphonate (E. Baer and H. O. L. Fischer, *J. Amer. Chem. Soc.*, (1948), 70, 609) with imidazole or a substituted imidazole at elevated temperature (of the order of 80° C.) in a suitable dry polar solvent (e.g. acetonitrile), followed by an acidic work-up to remove the glycol protecting-group.

Alternatively, compounds of general structure XII having the R-stereochemistry in which Ar, Ar$^1$, Alk$^1$ and Alk$^2$ are defined as hereinbefore, with the proviso that Ar=Ar$^1$ and Alk$^1$=Alk$^2$,

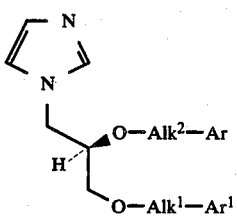

may be obtained by reacting the corresponding R-diol XIII

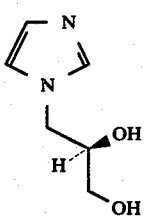

with 2 equivalents of a compound of general formula III in which Ar, Alk$^2$, and Q$^1$ are defined as hereinbefore. The reaction is preferably carried out in the presence of a suitable strong base, such as sodium hydride in an anhydrous aprotic solvent under an inert atmosphere.

The R-diol of structure XIII may be obtained by the cleavage of the R-benzyl ether of structure XIV. The reaction is preferably carried out under an atmosphere

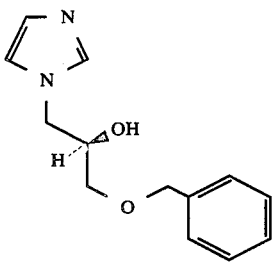

XIV of hydrogen in the presence of a suitable catalyst such as palladium absorbed onto charcoal in a suitable solvent (e.g. ethanol).

The benzyl ether of structure XIV may be obtained by reacting the compound of structure XV with imidazole

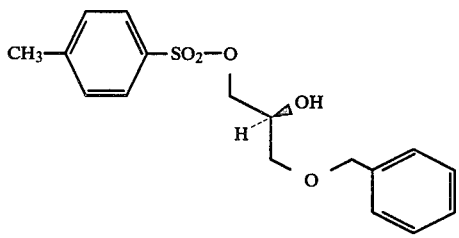

XV or a substituted imidazole at elevated temperature (of the order of 80° C.) in a suitable dry polar solvent (e.g. acetonitrile).

The tosylate of structure XV may be obtained by reacting the diol of structure XVI with p-toluene sulphonyl chloride using standard conditions.

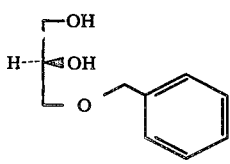

XVI

The diol of structure XVI may be obtained from the S-isopropylidene ether of structure XVII by acid hydrolysis

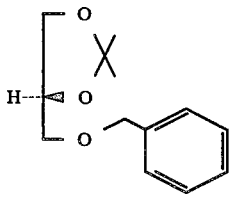

XVII using a suitable mineral acid (e.g. hydrochloric acid) in a suitable solvent such as acetone.

Finally, the compound of structure XVII may be obtained from S-α,β-isopropylidene glycol by reaction with a benzyl halide. The reaction is preferably carried out in the presence of a suitable strong base (e.g. sodium hydride) in an anhydrous aprotic solvent under an inert atmosphere.

The compounds according to the invention may be administered by any suitable route, preferably in the form of a pharmaceutical composition adapted to such route, and in a dose effective for the treatment intended.

Accordingly, the invention provides a pharmaceutical composition comprising one or more compounds according to the invention in association with one or more non-toxic, pharmaceutically acceptable carriers and/or diluents and/or adjuvants and if desired other active ingredients. The composition may for example be applied orally or by injection.

For oral administration, the pharmaceutical composition may take the form of, for example, a tablet, capsule, suspension or liquid. The pharmaceutical composition is preferably made in the form of a dosage unit contained in a particular amount of the active ingredient. Examples of such dosage units are tablets or capsules. These may with advantage contain an amount of active ingredient from 5 to 250 mg preferably 25 to 150 mg. A suitable daily dose for a mammal may vary widely depending on the condition of the patient and other factors. However, a dose of from 0.1 to 300 mg/kg body weight, particularly 0.5 to 10 mg/kg body weight preferably 5 mg to 10 mg/kg weight may be appropriate.

The active ingredient may also be administered by injection as a composition wherein, for example, saline, dextrose or water for injection may be used as a suitable carrier. A suitable daily dose of about 0.1 to 100 mg per kg body weight injected per day in multiple doses depending on the disease being treated. A preferred daily dose would be from 1–30 mg/kg body weight.

As indicated, the dose administered and the treatment regimen will be dependent, for example, on the disease, the severity thereof, on the patient being treated and his response to treatment and therefore may be widely varied.

The pharmaceutical compositions may be prepared by techniques well known in the art and described, interalia, in Remington's Pharmaceutical Science, Mach Publishing Co., Easton, Penn., 1965.

The following examples illustrate the invention:

EXAMPLE 1

1-[2-[(4-Methoxyphenyl)methoxy]-3-[(4-methoxyphenyl)methoxylpropyl]-1H-imidazole (a) 2,3-Epoxypropyl-4-methoxybenzyl ether A solution of 4-methoxybenzyl alcohol (800 g, 5.8M) in dry tetrahydrofuran (1200 ml) was added dropwise to a stirred slurry of sodium hydride (280 g of a 60% dispersion in oil, 7.8M) in dry tetrahydrofuran (600 ml) at −5° C. and under a gentle stream of dry nitrogen. The mixture was allowed to warm up to room temperature and stirred until hydrogen evolution ceased. The resulting slurry of the sodium alkoxide was cooled to −5° C. and treated with epibromohydrin (860 g, 6.3M) at a rate such that the temperature remained below 5° C. The reaction mixture was allowed to warm gradually to room temperature and left stirring for 12 hours.

The final mixture was filtered and washed with methanol. The combined filtrate and washings were evaporated to dryness under reduced pressure to afford the crude product (250 g). Further purification of this crude product by column chromatography (silica gel, 25% hexane in chloroform to 10% methanol in chloroform) afforded 2,3-epoxypropyl-4-methoxybenzyl ether as a pale yellow oil.

$^1$H-NMR (δ-CDCl$_3$) : 2.70 (m, 2H), 3.20 (m, 1H), 3.65 (m, 2H), 3.37 (s, 3H), 4.73 (s, 2H) and 7.15 (q, 4H).

(b)
1-[2-Hydroxy-3-[(4-methoxyphenyl)methoxy]propyl]-1H-imidazole 2,3-Epoxypropyl-4-methoxybenzyl ether (100 g, 0.725M) in dry tetrahydrofuran (200 ml) was treated with imidazole (44.4 g, 0.765M) and heated under reflux for 16 hours. The solution was filtered and the solvent was evaporated off under reduced pressure to give a brown solid which was recrystallised from 10% water-propan-1-ol to give 1-[2-Hydroxy-3-[(4-methoxyphenyl)methoxy]propyl]-1H-imidazole (83 g) as a colourless crystalline solid, m.p. 96°–98° C.

(c)
1-[2-[(4-methoxyphenyl)methoxy]-3-[(4-methoxyphenyl)methoxy]propyl]-1H-imidazole A solution of 1-[2-hydroxy-3-[(4-metoxyphenyl)methoxy]propyl]-1H-imidazole (206 g, 0.79M) in dry tetrahydrofuran (3700 ml) was added dropwise to a stirred slurry of sodium hydride (38 g of a 60% dispersion in oil, 0.95M; prewashed with pentane) in dry tetrahydrofuran (200 ml) at below 5° C. and under a gentle stream of dry nitrogen. The resulting mixture was stirred at room temperature for 1 hour and 4-methoxybenzyl chloride (123.2 g, 0.79M) in dry tetrahydrofuran (100 ml) was added. The resulting mixture was stirred at room temperature, protected from light, for 3 days.

The crude mixture was evaporated to dryness under reduced pressure, taken up in ethyl acetate (800 ml) and filtered. The solvent was evaporated off under reduced pressure to afford a brown oil which was purified by column chromatography (silica gel, 5% hexane in t-butylmethyl ether to 5% methanol in t-butylmethyl ether to give 1-[2-[(4-methoxyphenyl)methoxy]-3-[(4-methoxyphenyl)methoxy]propyl]-1H-imidazole as a colourless crystalline solid (169 g), m.p. 73°–74° C. (acetone-hexane). Analysis found: C,68.84; H,6.88; N,7.21; $C_{22}H_{26}N_2O_4$ requires: C,69.09; H,6.85; N,7.32%.

$^1$H-NMR ($\delta$-CDCl$_3$): 3.41 (m, 2H), 3.55 (m, 1H), 3.77, 3.79 (2 singlets, 6H) 4.06 (m, 2H), 4.43 (m, 4H) and 6.70–7.50 (m, 11H).

EXAMPLES 2–40

The following imidazole derivatives were prepared in the same manner as described for Example 1, by using the appropriately substituted benzyl alcohol/mercaptan (Ar$^1$CH$_2$YH) and the appropriate benzylic compound (ArCH$_2$Z) Table 1 shows the structures of the aryl groups (Ar$^1$ and Ar), the heteroatom (Y) and the nucleofuge (Z) together with proton n.m.r. spectral data for the products. Where obtained melting points (m.p.) and analytical data for the compounds are also given.

TABLE 1

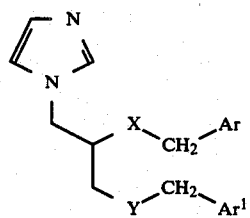

| Example No. | Z | X | Y | Ar$^1$ | Ar | NMR ($\delta$-CDCl$_3$) |
|---|---|---|---|---|---|---|
| 2$^a$ | Cl | O | O | —C$_6$H$_4$—OCH$_3$ | —C$_6$H$_5$ | 3.41(m,2H), 3.55(m,1H), 3.80(s,3H), 4.08(m,2H), 4.44(br.s,4H), and 6.70–7.50(m,12H) |
| 3 | Cl | O | O | —C$_6$H$_4$—OCH$_3$ | —C$_6$H$_4$—F | 3.41(m,2H), 3.55(m,1H), 3.80(s,3H), 4.07(m,2H), 4.44(s,4H), and 6.70–7.50(m,11H) |
| 4 | Cl | O | O | —C$_6$H$_4$—OCH$_3$ | —C$_6$H$_4$—Cl | 3.41(m,2H), 3.55(m,1H), 3.80(s,3H), 4.10(m,2H), 4.44(br.s,4H), and 6.70–7.50(m,11H) |
| 5 | Cl | O | O | —C$_6$H$_4$—OCH$_3$ | —C$_6$H$_4$—Cl (3-Cl) | 3.45(m,2H), 3.55(m,1H), 3.78(s,3H), 4.10(m,2H), 4.44(s,4H), and 6.70–7.50(m,11H) |
| 6 | Cl | O | O | —C$_6$H$_4$—OCH$_3$ | —C$_6$H$_4$—Cl (2-Cl) | 3.44(m,2H), 3.55(m,1H), 3.79(s,3H), 4.11(m,2H), 4.44(s,2H), 4.58(d,2H), and 6.70–7.50(m,11H) |

TABLE 1-continued

[Structure: imidazole-N-CH2-CH(X-CH2-Ar)-CH2-Y-CH2-Ar¹]

| Example No. | Z | X | Y | Ar¹ | Ar | NMR (δ-CDCl₃) |
|---|---|---|---|---|---|---|
| 7 | Cl | O | O | 4-OCH₃-C₆H₄- | 3,4-diCl-C₆H₃- | 3.44(m,2H), 3.55(m,1H), 3.80(s,3H), 4.09(m,2H), 4.44(s,4H), and 6.70–7.50(m,10H) |
| 8 | Cl | O | O | 4-OCH₃-C₆H₄- | 3,4-diCl-C₆H₃- | 3.44(m,2H), 3.55(m,1H), 3.79(s,3H), 4.15(m,2H), 4.44(s,2H), 4.52(d,2H), and 6.70–7.50(m,10H) |
| 9 | Cl | O | O | 4-OCH₃-C₆H₄- | 2,3-diCl-C₆H₃- | 3.46(m,2H), 3.55(m,1H), 3.80(s,3H), 4.11(m,2H), 4.44(s,2H), 4.77(s,2H), and 6.70–7.50(m,10H) |
| 10 | Cl | O | O | 4-OCH₃-C₆H₄- | 2,4-diCl-C₆H₃- | 3.41(m,2H), 3.60(m,1H), 3.80(s,3H), 4.11(m,2H), 4.39(d,2H), 4.44(s,2H), and 6.70–7.50(m,10H) |
| 11 | Br | O | O | 4-OCH₃-C₆H₄- | 4-Br-C₆H₄- | 3.45(m,2H), 3.55(m,1H), 3.78(s,3H), 4.10(m,2H), 4.44(s,4H), and 6.70–7.50(m,11H) |
| 12 | Cl | O | O | 4-OCH₃-C₆H₄- | 4-CH₃-C₆H₄- | 2.32(s,3H), 3.40(m,2H), 3.55(m,1H), 3.80(s,3H), 4.05(m,2H), 4.43(s,4H), and 6.70–7.50(m,11H) |
| 13 | Cl | O | O | 4-OCH₃-C₆H₄- | 2-CH₃-C₆H₄- | 2.22(s,3H), 3.40(m,2H), 3.55(m,1H), 3.80(s,3H), 4.10(m,2H), 4.43(s,4H), and 6.70–7.50(m,11H) |
| 14 | Cl | O | O | 4-OCH₃-C₆H₄- | 4-C(CH₃)₃-C₆H₄- | 1.30(s,9H), 3.40(m,2H), 3.55(m,1H), 3.79(s,3H), 4.10(m,2H), 4.43(s,4H), and 6.70–7.50(m,11H) |
| 15 | Cl | O | O | 4-OCH₃-C₆H₄- | 2-OCH₃-C₆H₄- | 3.40(m,2H), 3.55(m,1H), 3.76(s,3H), 3.79(s,3H), 4.08(m,2H), 4.43(br.s,4H), and 6.70–7.50(m,11H) |

TABLE 1-continued

[Structure: imidazole-N-CH₂-CH(CH₂-X-CH₂-Ar)(CH₂-Y-CH₂-Ar¹)]

| Example No. | Z | X | Y | Ar¹ | Ar | NMR (δ-CDCl₃) |
|---|---|---|---|---|---|---|
| 16 | Cl | O | O | 4-OCH₃-C₆H₄- | 2-OCH₃-C₆H₄- | 3.40(m,2H), 3.55(m,1H), 3.77(s,3H), 3.78(s,3H), 4.10(m,2H), 4.43(s,2H), 4.54(s,2H), and 6.70–7.50(m,11H) |
| 17 | Cl | O | O | 4-OCH₃-C₆H₄- | 3,4-di-OCH₃-C₆H₃- | 3.42(m,2H), 3.55(m,1H), 3.81(s,3H), 3.83(s,3H), 3.86(s,3H), 4.10(m,2H), 4.39(d,2H), and 6.70–7.50(m,10H) |
| 18 | Cl | O | O | 4-OCH₃-C₆H₄- | 2,4-di-OCH₃-C₆H₃- | 3.42(m,2H), 3.55(m,1H), 3.73(s,6H), 3.79(s,3H), 4.10(dd,2H), 4.43 (s,2H), 4.50(s,2H), and 6.70–7.50(m,10H). |
| 19 | Cl | O | O | 4-OCH₃-C₆H₄- | 3,4,5-tri-OCH₃-C₆H₂- | 3.41(m,2H), 3.55(m,1H), 3.80(s,9H), 3.82(s,3H), 4.08(m,2H), 4.39(d,2H), 4.45(s,2H), 6.40(s,2H), and 6.70–7.50(m,7H). |
| 20[b] | Cl | O | O | 4-OCH₃-C₆H₄- | 3,4-methylenedioxyphenyl | 3.39(m,2H), 3.55(m,1H), 3.80(s,3H), 4.08(m,2H), 4.33(d,2H), 4.43(s,2H), 5.92(s,2H), and 6.70–7.50(m,10H) |
| 21 | Cl | O | O | 4-OCH₃-C₆H₄- | 6-Cl-3,4-methylenedioxyphenyl | 3.43(m,2H), 3.65(m,1H), 3.81(s,3H), 4.10(m,2H), 4.35–4.75(m,4H), 5.96(s,2H) and 6.65–7.55(m,9H). |
| 22[c] | Cl | O | O | 4-OCH₃-C₆H₄- | 4-OEt-C₆H₄- | 1.38(t,3H), 3.15–3.45(m,2H), 3.50(m,1H), 3.78(s,3H), 3.85–4.10(m,4H), 4.10–4.50(m,4H) and 4.55–7.45(m,11H). |
| 23 | Cl | O | O | 4-OCH₃-C₆H₄- | 4-OCH₂Ph-C₆H₄- | 3.38(m,2H), 3.55(m,1H), 3.39(s,3H), 4.10(m,2H), 4.43(m,4H), 5.04(s,2H), and 6.70–7.50(m,16H). |
| 24 | Br | O | O | 4-OCH₃-C₆H₄- | 4-CN-C₆H₄- | 3.42(m,2H), 3.55(m,1H), 3.80(s,3H), 4.10(m,2H), 4.45(m,4H), and 6.70–7.50(m,11H). |

TABLE 1-continued

Structure: Imidazole-N-CH2-CH(CH2-X-CH2-Ar)(CH2-Y-CH2-Ar¹)

| Example No. | Z | X | Y | Ar¹ | Ar | NMR (δ-CDCl₃) |
|---|---|---|---|---|---|---|
| 25[d] | Br | O | O | —⟨C₆H₄⟩—OCH₃ | —⟨C₆H₄⟩—COOEt | 1.36(t,3H), 3.43(m,2H), 3.47–3.76 (m,1H), 3.76(s,3H), 4.05(m,2H), 4.29–4.51(m,4H), 4.43(s,2H), 6.81–8.02 (m,11H) |
| 26 | Cl | O | O | —⟨C₆H₄⟩—OCH₃ | —⟨naphthyl⟩ | 3.40(m,2H), 3.55(m,1H), 3.78(s,3H), 4.10(m,2H), 4.41(s,2H), 4.89(d,2H), and 6.70–7.50(m,11H). |
| 27 | Cl | O | O | —⟨C₆H₄⟩—OCH₃ | —⟨pyridyl⟩ | 3.42(m,2H), 3.55(m,1H), 3.80(s,3H), 4.13(m,2H), 4.45(s,2H), 4.63(d,2H), and 6.70–8.60(m,11H). |
| 28 | Cl | O | O | —⟨C₆H₄⟩—OCH₃ | —⟨pyridyl⟩ | 3.46(m,2H), 3.55(m,1H), 3.80(s,3H), 4.13(m,2H), 4.45(s,2H), 4.63(d,2H), and 6.70–8.60(m,11H). |
| 29 | Cl | O | O | —⟨C₆H₄⟩—OCH₃ | —⟨furyl⟩ | 3.39(m,2H), 3.55(m,1H), 3.81(s,3H), 4.05(m,2H), 4.34(d,2H), 4.44(s,2H), 6.25(m,1H) and 6.70–7.45(m,9H). |
| 30 | Br | O | O | —⟨C₆H₄⟩—OCH₃ | —⟨thienyl⟩ | 3.39(m,2H), 3.55(m,1H), 3.81(s,3H), 4.05(m,2H), 4.20—4.65(m,4H) and 6.70–7.45(m,10H). |
| 31 | Cl | O | O | —⟨C₆H₃⟩(Cl)(Cl) | —⟨C₆H₄⟩—OCH₃ | 3.41(m,2H), 3.55(m,1H), 3.70(s,3H), 4.00(m,2H), 4.40(m,4H), and 6.60–7.50(m,10H). |
| 32 | Cl | O | O | —⟨C₆H₄⟩—OCH₃ (meta) | —⟨C₆H₄⟩—OCH₃ | 3.42(m,2H), 3.55(m,1H), 3.77(s,3H), 3.79(s,3H), 4.07(m,2H), 4.38(q,2H), 4.47(s,2H) and 6.70–7.45(m,11H) |
| 33 | Cl | O | O | —⟨methylenedioxyphenyl⟩ | —⟨C₆H₄⟩—OCH₃ | 3.10–3.60(m,3H), 3.79(s,3H), 4.11 (m,2H), 4.39(br.s,4H), 5.95(s,2H), and 6.60–7.45(m,9H) and 7.64(s,1H). |
| 34 | Cl | O | O | —⟨methylenedioxyphenyl⟩ | —⟨pyridyl⟩ | 3.45(m,2H), 3.75(m,1H), 4.11(m,2H), 4.36(d,2H), 4.52(s,2H), 5.93(s,2H), and 6.68–7.80(m,8H), and 8.55(m,2H). |

TABLE 1-continued

[Structure: imidazole-N-CH2-CH(X-CH2-Ar)-CH2-Y-CH2-Ar¹]

| Example No. | Z | X | Y | Ar¹ | Ar | NMR (δ-CDCl₃) |
|---|---|---|---|---|---|---|
| 35 | Br | O | S | 4-OCH₃-C₆H₄- | 4-OCH₃-C₆H₄- | 2.46(m,2H), 3.45(m,1H), 3.65(s,2H), 3.76(s,6H), 4.01(m,2H), 4.27(q,2H) and 6.60–7.45(m,11H). |
| 36 | Cl | O | O | 4-N(CH₃)₂-C₆H₄- | 4-OCH₃-C₆H₄- | 2.94(s,6H), 3.37–3.80(m,3H), 3.78(s,3H), 4.06(m,2H), 4.35(m,2H), 4.40(s,2H), 6.64–7.25(m,10H), and 7.45(s,1H). |
| 37 | Cl | O | O | 4-OCH₃-C₆H₄- | 4-OPh-C₆H₄- | 3.42(m,2H), 3.70(m,1H), 3.80(s,3H), 4.08(m,2H), 4.44(m,4H), and 6.70–7.50(m,16H). |
| 38 | Cl | O | O | 4-OCH₃-C₆H₄- | 3-CF₃-C₆H₄- | 3.43(m,2H), 3.65(m,1H), 3.75(s,3H), 4.05(m,2H), 4.43(m,4H), and 6.70–7.60(m,11H). |

[a] Analysis found: C, 71.30; H, 6.85; N, 8.01; $C_{21}H_{24}N_2O_3$ requires: C, 71.55; H, 6.89; N, 7.96%
[b] Analysis found: C, 66.28; H, 6.15; N, 6.96; $C_{22}H_{24}N_2O_5$ requires: C, 66.65; H, 6.06; N, 7.07%
[c] Melting point 43–45° C. Analysis found: C, 69.28; H, 7.05; N, 6.92; $C_{23}H_{28}N_2O_4$ requires: C, 69.67; H, 7.12; N, 7.07%
[d] Analysis found: C, 67.50; H, 6.60; N, 6.51; $C_{24}H_{28}N_2O_5$ requires: C, 67.91; H, 6.65; N, 6.60%

EXAMPLE 39

4-[[[1-(1H-imidazol-1-yl)-2-(4-methoxyphenyl)methoxy]ethoxy]methyl]benzoic acid

4-[[[1-(1H-imidazol-1-yl)-2-(4-methoxyphenyl)methoxy]ethoxy]methyl]benzoic acid, ethyl ester (Example 25, 12 g) was treated with a 10% ethanolic solution of potassium hydroxide (30 ml) and stirred at 18° C. for 24 hours. The solvent was evaporated off under reduced pressure and the residue was treated with water (100 ml). Acetic acid (5 ml) was added to adjust the pH of the solution to pH 5 and the solution was extracted with dichloromethane. The combined extracts were dried (Na₂SO₄) and the solvent was evaporated off under reduced pressure to give the crude product which was further purified by chromatography (silica gel, 10% ethanol in dichloromethane) to give 4-[[[1H-imidazol-1-yl)-2-(4-methoxyphenyl)methoxy]ethoxy]methyl]benzoic acid. Analysis found: C,65.53; H,6.16; N,6.79; $C_{22}H_{24}N_2O_5$. ½H₂O requires: C,65.17; H,6.21; N,6.91%

¹H-NMR (δ-CDCl₃): 3.85–3.50 (m, 1H), 3.45 (m, 2H), 3.79 (s, 3H), 4.12 (m, 2H), 4.45 (s, 2H), 4.20–4.55 (m, 2H), 6.82–7.29 (m, 8H), 7.99–8.09 (d, 2H), and 10.73 (s, 1H).

EXAMPLES 40,41

The following derivatives in which the imidazole ring is further substituted were prepared by the same procedure as used for Example 1, but using the appropriately substituted imidazole. Table 2 shows the substitution patern of the imidazole together with proton n.m.r. spectral data for the products.

TABLE 2

[Structure: 2-R¹,4-R²-imidazol-1-yl-CH2-CH(O-CH2-C6H4-OCH3)-CH2-O-CH2-C6H4-OCH3]

| Example No. | R¹ | R² | NMR (δ-CDCl₃) |
|---|---|---|---|
| 40 | —CH₃ | H | 2.30(s,3H), 3.45(m,2H), 3.60(m,1H), 3.75(s,3H), 3.78(s,3H), 3.95(m,2H), 4.30(m,2H), 4.43(s,2H), and 6.60–7.40(m,10H). |
| 41 | —CH₂CH₃ | —CH₃ | 1.25(t,3H), 2.15(s,3H), 2.60(q,4H), 3.45(m,2H), 3.50–4.00(2xs,m,8H), 4.06(m,1H), 4.25–4.60 (m,4H), 6.45(s,1H), and 6.60–7.35(m,11H). |

EXAMPLE 42

1-[3-[(4-Methoxyphenyl)methoxy]-2-[3-(4-methoxyphenyl)propyl-1-oxy]propyl]-1H-imidazole (a) 3-(4-Methoxyphenyl)propan-1-ol, methane sulphonate Methyl sulphonyl chloride (12.5 g, 0.11M) was added dropwise to a stirred solution of p-methoxyphenylpropanol (16.6 g, 0.10M) in dichloromethane (60 ml)/pyridine (20 ml) at 0° C. The reaction mixture was maintained at 0° C. for 12 hours, then diluted with dichloromethane (250 ml) and washed with hydrochlorid acid ($5 \times 50$ ml of 5M.1$^{-1}$). The solution was washed with water, dried (MgSO$_4$) and the solvent was evaporated off under reduced pressure to give 3-(4-methoxyphenyl)propan-1-ol, methane sulphonate (20 g), as a colourless crystalline solid, m.p. 41–42° C. (pentane).

(b)
1-[3-[(4-Methoxyphenyl)methoxy]-2-[3-(4-methoxyphenyl)propyl-1-oxy]propyl]-1H-imidazole.

1-[2-Hydroxy-3-[(4-methoxyphenyl)methoxy]propyl]-1H-imidazole (5.24 g, 0.02M; prepared as in Example 1 (a)) was added to a stirred slurry of sodium hydride (0.88 g of a 60% dispersion in oil, 0.022M) in dry dimethoxyethane (45 ml) containing dry dimethylsulphoxide (2 ml) under a gentle stream of dry nitrogen. The resulting mixture was stirred at room temperature for 0.5 hours and then treated with 3-(4-methoxyphenyl)propan-1-ol, methane sulphonate (5.37 g, 0.022M) and stirred at 70° C. for a further 18 hours. The solvent was evaporated off under reduced pressure and the residue was dissolved in ethyl acetate (300 ml), washed with water ($4 \times 50$ ml) and dried (MgSO$_4$). The solvent was evaporated off under reduced pressure to give the crude product which was further purified by chromatography (silica gel, 10% pentane in chloroform) to give 1-[3-[(4-methoxyphenyl)methoxy]-2-[3-(4-methoxyphenyl)propyl-1-oxy]propyl]-1H-imidazole (1.3 g) as a colourless oil.

$^1$H-NMR ($\delta$-CDCl$_3$): 1.67–1.95 (m, 2H), 2.55 (t, 2H), 3.10–3.65 (m, 5H), 3.77 (s, 3H), 3.80 (s, 3H), 3.90–4.15 (m, 2H), 4.43 (s, 2H), and 6.60–7.50 (m, 11H).

EXAMPLE 43

1-[3-[(4-Methoxyphenyl)methoxy]-2-[3(4-methoxyphenyl)-2-methylpropyl-1-oxy]propyl-1H-imidazole was prepared by the same procedure as for Example 42 but using 3-(4-methoxyphenyl)-2-methylpropanol, methane sulphonate.

EXAMPLE 44

1-[3-[3-(4-Methoxyphenyl)propyl-1-oxy]2-[(4-methoxyphenyl)methoxy]propyl]-1H-imidazole.

(a) 2,3-Epoxypropyl-4-methoxyphenylpropyl ether

4-Methoxyphenylpropanol (15 g, 0.090M) was added dropwise to a stirred slurry of sodium hydride (4.0 g of a 60% dispersion in oil, 0.10M) in dry tetrahydrofuran (100 ml) and the stirred mixture was heated at 60° C. for 1 hour under a gentle stream of dry nitrogen. On cooling, epibromohydrin (12.8 g 0.0934M) was added and the mixture was stirred at ambient temperature for 65 hours. The solvent was evaporated off under reduced pressure and the residue was treated with water (800 ml) and extracted with dichloromethane. The combined extracts were dried (Na$_2$SO$_4$) and the solvent was evaporated off under reduced pressure to give the crdue product which was further purified by chromotography (silica gel, dichloromethane) to give 2,3-epoxypropyl-4-methoxyphenylpropyl ether as a colourless oil.

H-NMR ($\delta$-CDCl$_3$): 1.6–2.1 (m, 2H), 2.5–2.9 (m, 4H), 3.0–3.4 (m, 1H), 3.3–3.7 (m, 4H), 3.77 (s, 3H), 6.7–7.1 (q, 4H).

(b)
1-[2-Hydroxy-3-[3-(4-methoxyphenyl)propyl-1-oxy]propyl]-1H-imidazole 2,3-Epoxypropyl-4-methoxyphenylpropyl ether (12 g, 0.054M) in dry acetonitrile (200 ml) was treated with imidazole (18 g, 0.265M) and heated under reflux for 16 hours. The solvent was evaporated off under reduced pressure and the residue was treated with water (800 ml) and extracted with dichloromethane. The combined extracts were dried (Na$_2$SO$_4$) and the solvent was evaporated off under reduced pressure to give the crude product which was further purified by chromatography (silica gel, chloroform) to give 1-[2-hydroxy-3-[3-(4-methoxyphenyl)propyl-1-oxy]propyl]-1H-imidazole as a colourless oil.

(c)
1-[3-[3-(4-Methoxyphenyl)propyl-1-oxy]-2-[(4-methoxyphenyl)methoxy]propyl]-1H-imidazole A solution of 1-[2-hydroxy-3-[3-(4-methoxyphenyl)propyl-1-oxy]propyl]-1H-imidazole (20 g, 0.069M) in dry tetrahydrofuran (60 ml) was added dropwise to a stirred slurry of sodium hydride (2.85 g of a 60% dispersion in oil 0.0715M) and stirred at 0° C. for 15 minutes under a stream of dry nitrogen and then allowed to warm up to room temperature. The resulting mixture was stirred at room temperature for 1 hour and then heated under reflux for 1 hour under a stream of dry nitrogen. The solution was cooled to 15° C. and treated dropwise with 4-methoxybenzyl chloride (11 g, 0.071M) and stirred at ambient temperature for 65 hours in an inert atmosphere. The solvent was evaporated off under reduced pressure and the residue was treated with water (800 ml) and extracted with dichloromethane. The combined extracts were dried (Na$_2$SO$_4$) and the solvent was evaporated off under reduced pressure to give the crude product which was further purified by chromatography (silica gel, chloroform) to give 1-[3-[3-(4-methoxyphenyl)propyl-1-oxy]-2-[(4methoxyphenyl)methoxy]propyl]-1H-imidazole as a pale yellow oil.

$^1$H-NMR ($\delta$-CDCl$_3$): 1.7–2.1 (m, 2H), 2.4–2.8 (t, 2H), 3.2–3.5 (m, 6H), 3.78 (s, 6H), 3.9–4.2 (m, 2H), 4.3–4.4 (d, 2H), 6.70–7.30 (m, 10H), and 7.45 (s, 1H).

EXAMPLE 45

N-[(4-Methoxyphenyl)methyl]-$\alpha$-[[(4-methoxyphenyl)methoxylmethyl]-1H-imidazole-1-ethanamine (a)
$\alpha$-[[(4-Methoxyphenyl)methoxy]methyl]-1H-imidazole-1-ethanol,4-methylbenzenesulphonate 4-Toluene sulphonyl chloride (18.0 g, 0.094M) was added in portions to a stirred solution of 1-[2-hydroxy-3-[(4-methoxyphenyl)methoxy]propyl]-1H-imidazole (3.14 g, 0.12M; prepared as in Example 1 (b)) in dry pyridine (100 cm$^3$)/dimethoxyethane (60 cm$^3$) at 0° C. over 0.5 hours. The solution was stirred at 0° C. for 4 hours. The reaction mixture was poured into ethyl acetate (1200 ml), washed with water ($4 \times 200$ ml) and dried (MgSO₄). The solvent was evaporated off under reduced pressure to give the crude product as a yellow oil which was further purified by chromatography (silica gel, 10% ethanol in chloroform) to give α-[[(4-Methoxyphenyl)methoxy)methyl]-1H-imidazole-1-ethanol,4-methylbenzenesulphonate as a colourless crystalline solid (17 g), m.p. 130°–131° C. (ether-ethanol).

(b)
1-[2-azido-3-[(4-Methoxyphenyl)methoxy]propyl]-1H-imidazole.

A solution of α-[[(4-Methoxyphenyl)methoxy]methyl]-1H-imidazole-1-ethanol,4-methylbenzenesulphonate (6.39 g, 0.015M) dry dimethylformamide (30 ml) was treated with sodium azide (1.69 g, 0.0225M) and heated at 70° C. for 16 hours. The solvent was evaporated off under reduced pressure and the residue was dissolved in ethyl acetate, washed with water and dried (MgSO₄). The solvent was evaporated off under reduced pressure to give the crude product which was further purified by chromatography (silica gel, 10% ethanol in chloroform) to give 1-[2-azido-3-[(4-methoxyphenyl)methoxy]-2-azido]propyl]-1H-imidazole (3.6 g) as a pale yellow oil.

¹H-NMR (δ-CDCl₃): 3.45 (m, 2H), 3.60 (m, 1H), 3.75 (s, 3H), 4.00 (m, 2H), 4.45 (s, 2H), and 6.70–7.45 (m, 7H).

(c)
1-[2-amino-3-[(4-Methoxyphenyl)methoxy]propyl]-1H-imidazole.

A solution of 1-[2-azido-3-[(4-methoxyphenyl)methoxy[propyl[-1H-imidazole (5.1 g, 0.018M) in dry tetrahydrofuran (10 ml) was added dropwise to a stirred slurry of lithium aluminium hydride (0.68 g, 0.018M) in dry tetrahydrofuran (40 ml) at room temperature under a stream of dry nitrogen. When the addition was complete the reaction mixture was heated under reflux for 18 hours. The solvent was evaporated off under reduced pressure and the residue was extracted with ethyl acetate, washed with saturated aqueous ammonium chloride solution and dried (MgSO₄). The solvent was evaporated off under reduced pressure to give 1-[2-amino-3-[(4-methoxyphenyl)methoxy]propyl]-1H-imidazole as an oil (3.6 g) which was used directly without further purification.

¹H-NMR (δ-CDCl₃): 1.44 (br.s, 2H), 3.29 (br.s, 3H), 3.80 (s, 3H), 3.96 (m, 2H), 4.44 (s, 2H) and 6.60–7.45 (m, 7H).

(d)
N-[(4-Methoxyphenyl)methyl]-α-[[4-methoxyphenyl)methoxy]methyl]-1H-imidazole-1-ethanamine.

A solution of 1-[2-amino-3-[(4-methoxyphenyl)methoxy]propyl]-1H-imidazole (1.70 g, 0.0065M) in dry acetonitrile (10 ml) containing triethylamine (0.5 ml) was treated with 4-methoxybenzyl chloride (1.12 g, 0.0072M) and heated under reflux for 18 hours under a stream of dry nitrogen. The solvent was evaporated off under reduced pressure and the residue was extracted with ethyl acetate, washed with saturated aqueous sodium hydrogen carbonate solution and dried (MgSO₄). The solvent was evaporated off under reduced pressure to give the crude product as an oil which was further purified by chromatography (silica gel), 10% ethanol in chloroform) to give N-[(4-methoxyphenyl)methyl]-α-[[(4-methoxyphenyl)methoxy]methyl]-1H-imidazole-1-ethanamine (0.09 g ) as a pale yellow oil.

¹H-NMR (δ-CDCl₃): 1.95 (broad s, 1H), 2.95 (m, 1H), 3.26 (m, 2H), 3.68 (s, 2H), 3.78 (s, 3H), 3.79 (s, 3H), 3.98 (d, 2H), 4.40 (s, 2H) and 6.55–7.45 (m, 11H).

EXAMPLE 46

1-[3-[(4-Methoxyphenyl)methoxy]-2-[[(4-methoxyphenyl)methyl]thio]propyl-1H-imidazole A solution of 4-methoxybenzyl mercaptan (1.65 g, 0.0107M) in dry dimethoxyethane (5 ml) was added dropwise to a stirred slurry of sodium hydride (0.52 g of a 50% dispersion in oil, 0.0107M) in dry dimethoxyethane (20 ml) containing dry dimethylsulphoxide (1 ml). The resulting mixture was stirred for 0.5 hours and then treated dropwise with a solution of α-[[(4-methoxyphenyl)methoxy]methyl]-1H-imidazole-1-ethanol, methylbenzenesulphonate (3.4 g, 0.0089M) prepared as in Example 45 (a) in dry dimethoxyethane (5 ml). The reaction mixture was stirred at room temperature for 2 hours and then at 60° C. for a further 18 hours. The solvent was evaporated off under reduced pressure and the residue was extracted with dichloromethane, washed with water and dried (MgSO₄). The solvent was evaporated off under reduced pressure to give the crude product as an oil which was further purified by chromatography (silica gel, 5% ethanol in chloroform) to give 1-[3-[(4-methoxyphenyl)methoxy]-2-[[(4-methoxyphenyl)methyl]thio]]propyl]-1H-imidazole (0.06 g) as a pale yellow oil.

¹H NMR (δ-CDCl₃): 2.90 (quintet, 1H), 3.36 (m, 3H), 3.53 (s, 2H), 3.77 (s, 3H) and 3.79 (s, 3H), 4.06 (m, 2H), 4.39 (s, 2H) and 6.60–7.45 (m, 11H).

The compound of Example 1 may be prepared as the two optical isomers (R-and S- forms) which are described as Examples 47–48.

EXAMPLE 47

S-1-[2-[(4-Methoxyphenyl)methoxy]-3-[(4-methoxyphenylmethoxy]propyl]-1H-imidazole (a) D-α,β-Isopropylidene glycerol, 4-methylbenzenesulphonate was prepared from S-α,β-isopropylidene glycerol and p-toluene sulphonyl chloride by the method of E. Baer and H.O.L. Fischer (*J. Amer. Chem. Soc.*, (1948), 70, 609).

(b) S-1-(2,3-Dihydroxypropyl)-1H-imidazole

A solution of R-α,β-isopropylidene glycerol, 4-methylbenzenesulphonate (4.5 g, 0.016M) in acetonitrile (5 ml) was treated with imidazole (3.21 g, 0.047M) and heated under reflux for 18 hours. The solvent was evaporated off under reduced pressure and the residue was dissolved in dichloromethane (150 cm³), washed with water and dried (MgSO₄). The resulting crude protected imidazole propane-diol was then treated with hydrochloric acid (3 ml of 5 Molar) and heated at 60° C. for 1.5 hours. The excess hydrochloric acid was evaporated off under reduced pressure to give S-1-(2,3-dihydroxypropyl)-1H-imidazole,hydrochloride as a hygroscopic solid.

¹H-NMR (δ-(CD₃)₂SO): 3.0–4.5 (m, 7H), 7.6–7.8 (m, 2H), 9.1 (s, 1H), (c) A solution of S-1-(2,3-dihydroxypropyl)-1H-imidazole, hydrochloride (0.82 g, 0.005M) in dry dimethylsulphoxide (2ml) was added to a stirred slurry of sodium hydride (0.79 g of a 50% dispersion in oil, 0.0165M) in dimethoxyethane (15 ml) at 0° C. under a stream of dry nitrogen. The reaction mixture was stirred at 18° C. for 2 hours and then treated with a solution of 4-methoxybenzyl chloride (1.72 g, 0.011M) in dry dimethylsulphoxide (2 ml) and stirred for a further 18 hours. The solvent was evaporated off under reduced pressure and the residue was treated with water and extracted with ether. The combined ether extracts were washed with water, dried (MgSO$_4$), and the solvent was evaporated off under reduced pressure to give the crude product which was further purified by chromatography (silica gel, 10% ethanol in chloroform) to give S-1-[2-[(4-methoxyphenyl)methoxy]-3-[(4-methoxyphenyl)methoxy]propyl]-1H-imidazole, $[\alpha]_{589}^{27} -26.98°$.

EXAMPLE 48

R-1-[3-[(4-Methoxyphenyl)methoxy]-2-[(4-methoxyphenyl)methoxy]propyl]-1H-imidazole (a) S-1-benzyloxy-2,3-dihydroxypropane S-$\alpha,\beta$-Isopropylidene glycerol (2.53 g, 0.0191M) was added dropwise to a stirred slurry of sodium hydride (1.08 g of a 50% dispersion in oil, 0.021M) in dry dimethoxyethane (15 ml) containing dry dimethylsulphoxide (3 ml). The reaction mixture was stirred at room temperature for 0.25 hours and then treated with benzyl chloride (2.66 g, 0.021M). The reaction mixture was heated at 80° C. for 3 hours. The solvent was evaporated off under reduced pressure and the residue was treated with water and extracted with ether. The combined extracts were dried (MgSO$_4$) and the solvent was evaporated off under reduced pressure to give the crude S-$\alpha,\beta$-isopropylidene glycerol, benzyl ether. The crude product was dissolved in acetone (4 ml) and treated with hydrochloric acid (2 ml of 1 Ml$^{-1}$) and heated at 70° C. for 2 hours. The solvent was evaporated off under reduced pressure and the residue was dissolved in ethyl acetate (120 ml), washed with saturated aqueous sodium hydrogen carbonate solution and dried (MgSO$_4$). The solvent was evaporated off under reduced pressure to give the crude product which was further purified by chromatography (silica gel, 10% ethanol in chloroform) to give R-1-benzyloxy-2,3-dihydroxypropane (3.2 g) as an oil.

(b)
S-[(1-benzyloxy-2,3-dihydroxypropane),3-(4-methylphenyl)sulphonate p-Toluene sulphonyl chloride (6.86 g, 0.036M) was added in portions to a stirred solution of R-1-benzyloxy-2,3-dihydroxypropane (6.0 g, 0.033M) and dry pyridine (7 ml) in dry dimethoxyethane (22 ml) at −40° C. The reaction mixture was then kept at 0° C. for 18 hours. The solvent was evaporated off under reduced pressure and the residue was dissolved in ether (200 ml), washed with hydrochloric acid (3×20 ml of 1 Ml$^{-1}$), washed with saturated aqueous sodium hydrogen carbonate solution (2×20 ml) and dried (MgSO$_4$). The solvent was evaporated off under reduced pressure to give the crude product which was further purified by chromatography (silica gel—2% ethanol in chloroform) to give S[(1-benzyloxy-2,3-dihydroxypropane), 3-(4-methylphenyl)sulphonate (1.1 g) as an oil.

(c)
R-1-[1-(3-Benzyloxy-2-hydroxy)propyl]-1H-imidazole

A solution of S-(1-benzyloxy-2,3-dihydroxypropane), 3-(4-methylphenyl)sulphonate (2.5 g, 0.0072M) in dry acetonitrile (7 ml) was treated with imidazole (1.47 g, 0.0217M) and heated under reflux for 18 hours. The solvent was evaporated off under reduced pressure and the residue was treated with water and extracted with ethyl acetate. The combined extracts were dried (MgSO$_4$) and the solvent was evaporated off under reduced pressure to give the crude product which was further purified by chromatography (silica gel, 15% ethanol in chloroform) to give R-1-[1-(3-benzyloxy-2-hydroxy)propyl]-1H-imidazole (1.19 g).

(d) R-1-[1-(2,3-Dihydroxy)propyl]-1H-imidazole, hydrochloride

A mixture of R-1-(3-benzyloxy-2-hydroxypropyl)-1H-imidazole (1.0 g, 0.0043M) and 10% palladium on charcoal (0.3 g) in ethanol (12 ml) containing 5 drops of ethereal hydrogen chloride was stirred under an atmosphere of hydrogen for 24 hours. The solution was filtered and the solvent was evaporated off under reduced pressure. The residue was dissolved in ethanol and acidified with ethereal hydrogen chloride to give R-1-[1-(2,3-dihydroxy)propyl]-1H-imidazole, hydrochloride.

(e)
R-1-[2-[(4-methoxyphenyl)methoxy]-3-[(4-methoxyphenyl)methoxy]propyl]-1H-imidazole R-1-[1-(2,3-Dihydroxy)propyl]-1H-imidazole, hydrochloride was reacted with 4-methoxybenzyl chloride using the procedure described in Example 47 (c) to give R-1-[2-[(4-methoxyphenyl)methoxy]-3-[(4-methoxyphenyl)methoxy]propyl]-1H-imidazole, $[\alpha]_{589}^{27} +22.08°$.

BIOLOGICAL EVALUATION

The compounds of the invention have been tested by the following in vitro radioimmunoassays for their ability to inhibit thromboxane and affect prostacyclin production.

In vitro tests

Thromboxane production in Human Platelet Rich Plasma (a) Platelet rich plasma (prp) preparation Human venous blood was calculated from healthy male donors, who had denied any medication during the previous 14 days. Nine volumes of blood were mixed with one volume of 3.24% trisodium citrate. The citrated blood was centrifuged at 160 g for 10 mins. at 22° C. to obtain platelet rich plasma (prp). The platelets were then counted on a Coulter counter, and the platelet count was adjusted to 200,000 per $\mu$l with plasma.

(b) Thromboxane generation

The prp was then dispensed as aliquots into micro-Eppendorf tubes, maintained at 37° C. in a dry bath. The compounds, dissolved either in saline, ethanol, or dimethylsulphoxide, were added in duplicate to the prp aliquots to produce final concentrations in the range of 0.1-30 $\mu$g/ml. When ethanol and DMSO were used as the vehicle, triplicate controls containing the same percentage of vehicle as the test compounds were made. The final concentration of organic solvent was never more than 0.1%, which in previous experiments had no effect on TxB$_2$ generation.

Following a 10 min. incubation with test compounds or vehicle, collagen was added to produce a final concentration of 20 $\mu$g/ml. The tubes were then whirly-mixed for 15 seconds and replaced in the dry bath for a further 10 minutes, controls received saline instead of collagen. The reaction was then stopped by rapid centrifugation (15000 g for 3 mins). The plasma was removed and frozen at −29° C. until assayed.

(c) Assay of Thromboxane $B_2$

Briefly, 100 μl aliquots of the following, in 50 mM phosphate buffer+0.1% gelatin+thimerosal (pH 6.8) were incubated together for 16 hours at 4° C.: thromboxane $TxB_2$ (plasma extract or standards 50 to 10,000 pg/ml), [$^3$H]—$TxB_2$ (approximately 15,000 dpm) and anti-$TxB_2$ antiserum (0.5 μg/100 μl). The free and protein bound [$^3$H]—$TxB_2$ were separated by adsorption onto activated charcoal followed by centrifugation. 1.0 ml of the supernatant was added to an aqueous scintillation fluid, and the radioactivity present was counted in a liquid scintillation counter. The binding of [$^3$H]—$TxB_2$ in the absence of added $TxB_2$ was approximately 55%. The least amount of $TxB_2$ to be detected accurately in the plasma was 50 pg/ml. Cross reactivity with other prostaglandins is less than 0.005% except $PGD_2$ which is 1%.

Thus plasma samples were assayed to give a rough approximation of $TxB_2$ content. The plasma was then appropriately diluted and assayed in duplicate to give accurate values.

(d) Analysis of Results

The amount of $TxB_2$ generated by the collagen was calculated by subtracting mean values obtained for the saline stimulated platelets from the mean values obtained from the collagen stimulated platelets. Then the amount of $TxB_2$ generated in the presence of each concentration of compound was expressed as a % control and dose response curves were then constructed to determine the concentration of compound which produced a 50% inhibition. These values known as the $IC_{50}$ obtained for various compounds tested are given in Table 3 below.

TABLE 3

| COMPOUND (EXAMPLE NO) | ACTIVITY ($IC_{50} \times 10^6$ M) |
|---|---|
| 1 | 12 |
| 2 | 11 |
| 4 | 23 |
| 15 | 14 |
| 20 | 4 |
| 24 | 12 |
| 28 | 10 |
| 30 | 20 |
| 34 | 13 |
| 35 | 22 |

Prostacyclin Production in Cultured Aortic Endothelial Cells (a) Cell culture

Bovine aortic arch tissue was obtained from a local abattoir, and transported to the laboratory on ice. Arterial endothelial cells were obtained from the washed (phosphate buffered saline) aortic arch tissue by gentle scraping of the intima, within two hours of sacrifice. Cell suspensions were washed by centrifugation, resuspended, and propagated in Roswell Park Memorial Institute (RPMI) 1640 medium (Moore, G. E., J.A.M.A., (1967), 199, 519) 1640 medium+20% foetal calf serum (FCS)+antibiotics (1-2 doublings). The cells were then trypsinised, cloned by limiting dilution, selected colonies grown to confluence (3-4 passages), and stored in liquid nitrogen. When required, batches of cells were removed from store, resuscitated, and propagated in RPMI medium+10% FCS+antibiotics (passaged 6-15 times). At trypsinisation, representative cells from each passage were transferred to multiwell plates ($1 \times 10^5$ cells/well) and incubated for 3 days (final count $3.5 \times 10^5$ cells/well).

The medium in each well of the plate was exchanged for serum and antibiotic free RPMI 1640, and a time 0 sample (100 μl) taken. Drugs or vehicle were next added as required, and a further sample (800 μl) taken from each well after a 60 minute incubation at 37° C. with gentle shaking. Prostacyclin synthesis and release into the medium over this period was estimated using an RIA technique for 6-keto $PGF_{1\alpha}$, the stable metabolite of $PGI_2$ (New England Nuclear 6-keto $PGF_{1\alpha}$ RIA kit, Catalogue No. NEK 008).

(b) Assay of 6-keto $PGF_{1\alpha}$

Briefly, 100 μl aliquots in 50 mM phosphate buffer+0.1% gelatin+0.01% thimerosal (pH 6.8) of the following were incubated together for 16 hours at 4° C.: 6-keto $PGF_{1\alpha}$ (incubation medium extract or standards 10-1000 pg/0.1 ml), [$^3$H]-6-keto $PGF_{1\alpha}$ (approximately 15000 dpm) anti-6-keto $PGF_{1\alpha}$ antiserum. The free base and protein bound [$^3$H]-6-keto $PGF_{1\alpha}$ were separated by adsorption onto activated charcoal followed by centrifugation. 850 μl of the supernatant was added to an aqueous scintillation fluid, and the radioactivity present counted in a liquid scintillation counter. The binding of [$^3$H]-6-keto $PGF_{1\alpha}$ in the absence of added 6-keto $PGF_{1\alpha}$ was approximately 40%. The least amount of 6-keto $PGF_{1\alpha}$ to be detected accurately in the samples was 100 pg/ml. Cross reactivity with other prostaglandins was less than 0.3% except $PGE_2$ (2%) and $PGF_{2\alpha}$ (2.7%).

By means of exemplification the data obtained for the compound of Example 1 is given below in Table 4.

TABLE 4

| Effect of Example I on $PGI_2$ synthesis in cultured bovine arterial endothelial cells in vitro | | |
|---|---|---|
| Example I (μm) | Net $PGI_2$ synthesis (pg 6-keto $PGF_{1\alpha}$/60 min/$3.5 \times 10^5$ cells) | % Change |
| 0 | 120 | 0 |
| 2.6 | 125 | +4 |
| 7.8 | 130 | +8 |
| 26.0 | 106 | −12 |
| 78.0 | 135 | +12 |

CONCLUSION

Table 4 shows that at in vitro concentrations substantially in excess of those which inhibit platelet thromboxane synthetase, Example 1 has no significant effect on basal $PGI_2$ synthesis in cultured bovine aortic endothelial cells over an incubation period of 1 hour.

Inhibition of Platelet Aggregation in vitro

In addition to the above tests, platelet aggregation in citrated prop (prepared as above) against a variety of aggregating agents was measured turbidometrically in a Payton Dual Channel Aggregometer (method as described in G.V.R. Born, Nature, (1962), 194, 927).

Compounds of the invention tested in this way actively inhibited both collagen and arachidonic acid induced aggregation of human prp in a dose related fashion. Thus, for purposes of exemplification, in this respect compounds of Example 1 and Example 20 were clearly more active than aspirin, dipyridamole, or sulphinpyrazone (Table 5).

TABLE 5

| | I.C.$_{50}$ ($\mu$M) vs | |
|---|---|---|
| | COLLAGEN | ARACHIDONIC ACID |
| EXAMPLE 1 | 103 | 31 |
| EXAMPLE 20 | 89 | 24 |
| ASPIRIN | 106 | 56 |
| DIPYRIDAMOLE | >200 | >200 |
| SULPHINPYRAZONE | 173 | — |

In vivo model

The retired breeder male rat may be utilized any time from 24 hours to 6 months after receipt without prior fasting or manipulation. The assay has been demonstrated to give consistent results without regard to the time of day or season of the year. The test (as described in R. N. Saunders, T. S. Burns, M. R. Selzer and E. R. Waskawic, Lab. Animal Sci., (1977), 27, 757–761) consists of the oral administration of the investigative compound either dissolved in or suspended in propylene glycol 400 at 20 mg/kg to four retired breeder male rats (40 mg of compound required). Three hours from the time of administration, the rats are ether anaesthetized, the abdominal cavity exposed and one ml of blood is withdrawn into each of two syringes from the vena cava. The first syringe contains four ml of buffered citrate/formalin solution and the second syringe contains four ml of buffered citrate alone. The syringes are inverted, held at room temperature for 15 minutes and the contents are centrifuged at 170 g for 14 minutes. Platelet counts are obtained on the undiluted solutions by means of a hemacytometer under 430×phase-contrast microscopy. The platelet aggregate ratio is obtained by dividing the platelet count of the first syringe by that of the second syringe. A ratio of 1.0 would indicate that no platelet aggregates are present whereas ratios below 1.0 indicate the presence and degree of platelet aggregate formation which has occurred. If an aggregate ratio of 0.85 or greater is observed, the compound is considered active at the $P<0.05$ level (see statistical analysis attached). The untreated retired breeder rat has an aggregate ratio of 0.76±0.02 whereas a virgin rat of the same age, sex, strain and supplier has a ratio of 0.94±0.02. A compound found active at the screening dose may be further evaluated at lower doses to produce an ED$_{50}$ or the dose at which the aggregate ratio is half way returned to the virgin rat value.

TABLE 6
COMPARISON OF ANTIPLATELET ACTIVITY OF EXAMPLE 1 AND EXAMPLE 20 WITH THAT OF OTHER ANTI-AGGREGATORY AGENTS IN THE MALE BREEDER RAT

| Compound | EX$_{50}$ (3h post oral administration) |
|---|---|
| EXAMPLE 1 | 0.49 mg/kg |
| EXAMPLE 20 | 1.8 mg/kg |
| aspirin | 7.7 mg/kg |
| dipyridamole (Persantine) | 1.8 mg/kg |
| sulfinpyrazone (Anturane) | 4.1 mg/kg |

I claim:

1. A compound of the formula

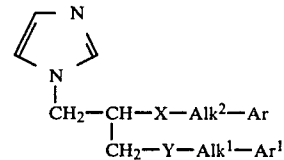

wherein
Ar is substituted phenyl having at least one substituent selected from the class comprising lower alkoxy, alkylenedioxy, carboxy and carboxyalkyl; and
Ar$^1$ is phenyl or substituted phenyl having at least one substituent selected from the class comprising halogen, lower alkyl, lower alkoxy, alkylenedioxy, aralkoxy, aryloxy, trihalomethyl, carboxy, carboxyalkyl, cyano, carboxamido, di-loweralkylamino, nitro and lower alkyl sulphonyl;
Alk$^1$ and Alk$^2$ are independently an alkylene group containing from 1 to 8 carbon atoms which may be substituted with one or more alkyl groups;
X and Y are independently —O—, —NH— or —S—; with the proviso that at least one of Ar and Ar$^1$ is phenyl substituted with alkylenedioxy
and acid addition salts thereof.

2. A compound according to claim 1 wherein Ar$^1$ is substituted phenyl having at least one substituent selected from the class comprising lower alkoxy, methylenedioxy, carboxy and carboxy lower alkyl.

3. A compound according to claim 2 wherein X and Y are —O—.

4. A compound according to claim 3 wherein the compound is 1-[2-[(4-methoxyphenyl)methoxy]-3-[3,4-methylenedioxyphenyl)methoxy]propyl]-1H-imidazole represented by the formula

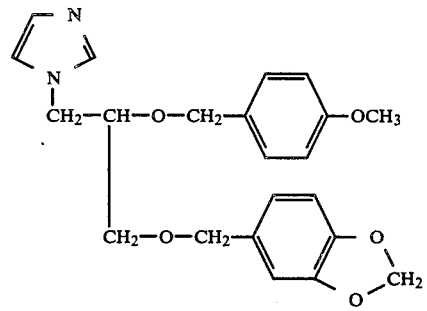

5. A compound according to claim 3 wherein is 1-[2-[(3,4-methylenedioxyphenyl)methoxy]-3-[(4-methoxyphenyl)methoxy]propyl]-1-H-imidazole represented by the formula

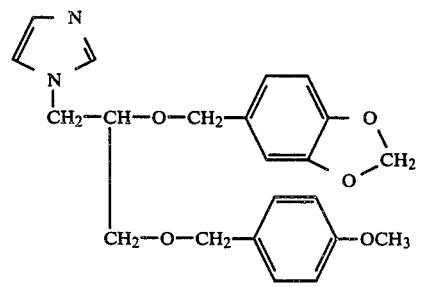

6. A pharmaceutical composition comprising a compound of claim 1 and a non-toxic pharmaceutically acceptable carrier.

7. A composition according to claim 6 comprising from 5 to 250 mg. of the compound.

* * * * *

UNITED STATES PATENT AND TRADEMARK OFFICE
CERTIFICATE OF CORRECTION

PATENT NO. : 4,636,518
DATED : January 13, 1987
INVENTOR(S) : Fellner, et al.

It is certified that error appears in the above-identified patent and that said Letters Patent are hereby corrected as shown below:

Column 9, Table 1, Example No. 6 reading "Cl O O" should read -- Br O O --.

Signed and Sealed this

Eighth Day of November, 1988

*Attest:*

DONALD J. QUIGG

*Attesting Officer*   *Commissioner of Patents and Trademarks*